Figure 1:
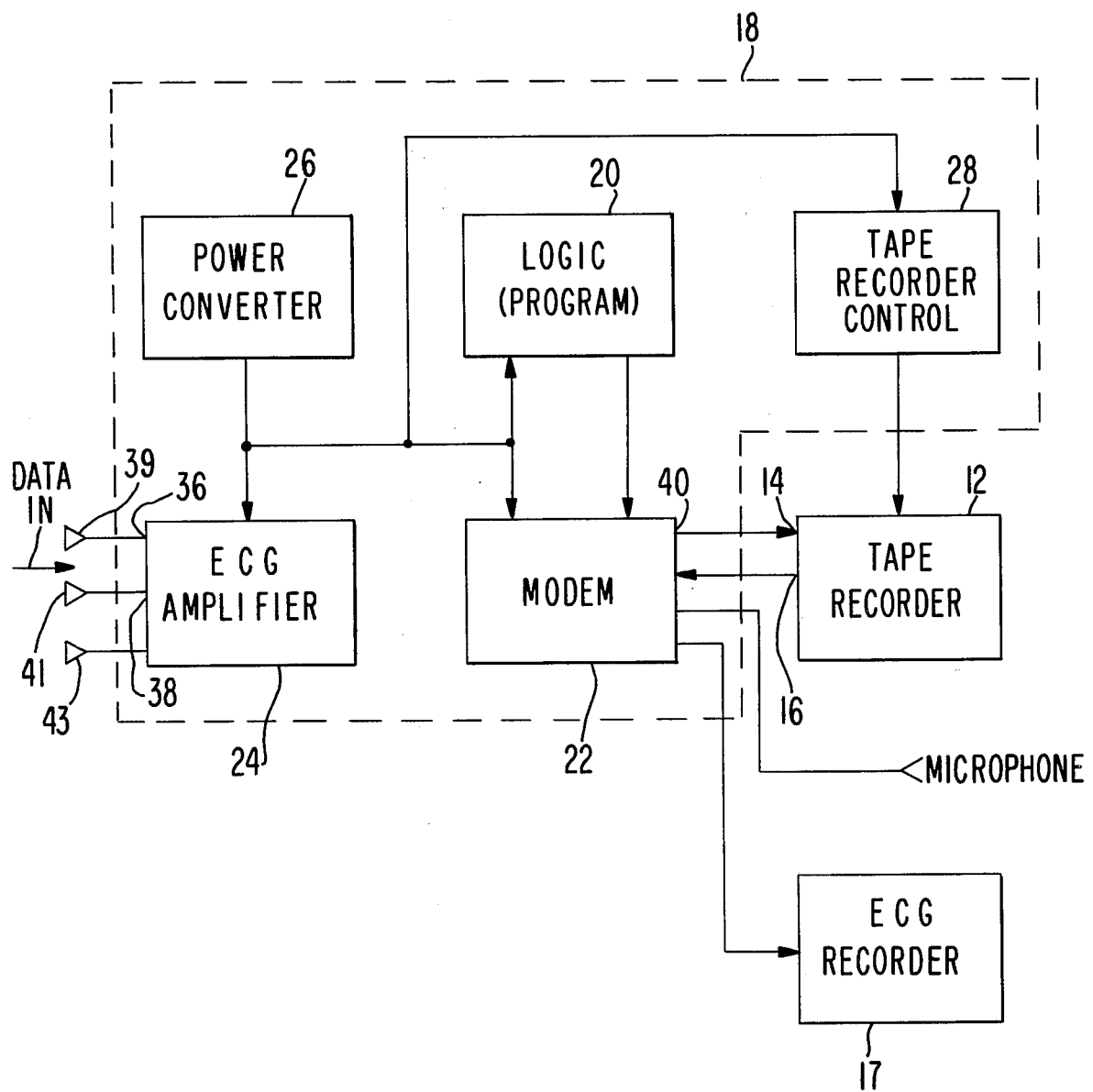

United States Patent [19]

Sibley et al.

[11] 4,183,354

[45] Jan. 15, 1980

[54] AMBULATORY ELECTROCARDIOGRAPHIC RECORDER

[75] Inventors: Alfred E. Sibley, Cupertino; Travis W. Winsor, Los Angeles; George F. Kinghorn, Saratoga, all of Calif.

[73] Assignee: Cardiodyne, Inc., Cupertino, Calif.

[21] Appl. No.: 816,403

[22] Filed: Jul. 18, 1977

[51] Int. Cl.² ............................................. A61B 5/04
[52] U.S. Cl. ................................ 128/711; 346/33 ME
[58] Field of Search .................. 128/2.06 G, 2.06 R, 128/2.06 A; 346/33 M

[56] References Cited

U.S. PATENT DOCUMENTS

| 3,524,442 | 8/1970 | Horth | 128/2.06 A |
| 3,651,280 | 3/1972 | Streckmann | 128/2.06 G |
| 3,934,267 | 1/1976 | Kosaka | 128/2.06 G |

*Primary Examiner*—William E. Kamm
*Attorney, Agent, or Firm*—Townsend and Townsend

[57] ABSTRACT

A recording device using a portable recorder, such as a small, battery powered tape recorder, carried on the person and provided with electrodes for attachment to the body of the user, the electrodes being operable to sense cardiac activity and to provide the input signals to a program module coupled with the recorder to cause the latter to be turned on and off at predetermined times so that it operates at predetermined periods for the purpose of recording samples of the user's cardiac activity sensed by the electrodes. The program module operates to amplify the input signals from the electrodes and to cause these signals to modulate a carrier wave signal suitable for recording by the tape or other recorder. The program module also is operable to demodulate the carrier wave signal when it is played back from the recorder to reproduce an accurate reproduction of the input signals from the electrodes. The demodulated signal can then be coupled to an ECG recorder and reproduced graphically, resulting in a standard ECG tracing which accurately represents what would have been obtained if the ECG recorder had been attached to the user at the time the initial recording was made. The program module also provides for a microphone input so that a user can record a verbal description of symptoms, environment and the like during the time of abnormal cardiac activity.

1 Claim, 2 Drawing Figures

AMBULATORY ELECTROCARDIOGRAPHIC RECORDER

This invention relates to improvements in the sensing and recording of electrocardiograms and, more particularly, to portable apparatus which can be carried on the person for sensing the electrocardiogram of the person and for recording cardiac activity at regular intervals and at other times, such as during abnormal cardiac activity.

BACKGROUND OF THE INVENTION

Certain individuals who have heart disease do not continuously exhibit abnormal cardiac activity, but rather they do so for brief periods of time at widely spaced intervals. During such periods, such an individual often experiences dizziness, fainting, breathing difficulties, or chest pains. It is extremely difficult for the physician to properly diagnose and treat such cases because symptoms rarely occur when the individual happens to be in the physician's office. See "Detection of Phantom Arrythmias and Evanescent Electrocardiograph Abnormalities", Corday, E. et al. JAMA 193:417, 1965. Two procedures are available for long-term observation of such individuals. The individual can be hospitalized and put under constant observation, including constant monitoring by automatic electronic equipment, or he can be fitted with a portable recording device which captures and records the electrocardiographic data associated with the transient abnormal cardiac event. Because of the expense and inconvenience of hospitalization, the latter procedure is often preferred.

Portable recording devices presently in use for this purpose record the ECG wave continuously, and the resulting mass of data must be thoroughly screened for unusual events and then analyzed for the significance of these events. This requires the use of very expensive and specialized data processing equipment and considerable time of a skilled operator. Moreover, a relatively large amount of data is collected because such equipment operates continuously. Much of this data is not usable because it is obtained when the individual is experiencing normal cardiac activity. U.S. Pat. No. 3,229,687 describes the design and operation of such specialized equipment.

SUMMARY OF THE INVENTION

The present invention proposes to provide a monitor device which reduces the amount of electrocardiographic data sensed and recorded by using a programmed or automatic ECG sampling unit which is operated periodically to collect data yet it can be placed under the control of the user, who usually knows when he or she is experiencing abnormal cardiac symptoms. In addition, this invention allows the physician to play back the greatly reduced quantity of data, together with the patient's own voice comments made during the recording episodes, upon his own ECG machine, with no specialized equipment or training being required. This procedure also permits considerable simplification of the design of the data recorder, thus reducing the weight, size and cost of this unit also. Although transient cardiac abnormalities usually persist for from fifteen minutes to an hour or more, a brief ECG recording of 5 to 20 seconds duration during such periods is usually adequate to detect, record and define the type of abnormality which is occurring.

In a preferred embodiment of the invention, the monitoring device of this invention includes a program module which is electrically coupled to a tape recorder which is portable and battery operated so that it can be worn or carried on the person. The function of the program module is to cause the recorder to be turned on at predetermined times and for predetermined intervals for the purpose of recording samples of an individual's electrocardiogram for later evaluation and analysis by a physician. The recording intervals and periods between their occurrence can be readily changed by the patient or his physician. The program module includes circuitry for amplifying the electrocardiographic signals taken from electrodes fixed to the body of the subject, and for causing these signals to modulate a carrier wave signal which is suitable for recording by the recorder, such as a small tape recorder. The program module also includes circuitry for demodulating the carrier wave signal when it is played back from the recorder for producing an accurate reproduction of the electrocardiographic signal as it was originally recorded. The demodulated signal is compatible with most ECG recorders and can be reproduced graphically during playback of the recorder so that a standard ECG tracing is obtained which accurately represents what would have been obtained had the ECG recorder been attached to the individual at the time that the tape recording was made.

The program module also contains a microphone input and appropriate control circuitry which enables the user of the device to record on the tape at any time he or she desires a verbal description of feelings, symptoms, environment, etc. which would be useful to the physician in the subsequent evaluation of the recorded data. Any such voice recording is always followed immediately by an ECG recording of a duration programmed in advance.

The program module can be set to automatically record a sample of the ECG signal at fixed intervals of time, for example, every 15 minutes, 30 minutes, 60 minutes or 120 minutes. The individual may override this program at any time and cause an extra data sample to be taken should he or she feel unusual symptoms or stress. The program module can be set to record samples of the ECG for fixed durations of, for example, 5 seconds, 10 seconds or 20 seconds. This capability greatly reduces the amount of data which need be recorded in order to obtain a good statistical picture of the behavior of an individual's heart throughout a time period of a few hours or several days. If, for instance, it is desired to sample a series of five or six heart cycles each hour for a 24-hour period, and the individual records an additional 5 special samples, the total duration of the recording will be 5×29 seconds, or 145 seconds. Thus, an ECG tracing about 12 feet long would contain all 29 samples of the individual's electrocardiogram at the standard ECG recording speed of 25 mm per second. It is, therefore, conceivable that an accurate record of a 24-hour period, with a high probability of containing the essential information on significant cardiac events, could be exhibited on a few feet of ECG tracing.

The primary object of this invention is to provide a portable recorder with appropriate circuitry to sense and record an individual's electrocardiogram identified by signals sensed by electrodes attached to the body, wherein the individual's cardiac activity can be monitored at periodic intervals and for predetermined times, yet can be recorded during periods of abnormal cardiac activity so as to provide an accurate evaluation of such activity notwithstanding the fact that the individual operates the tape recorder to provide a voice input or sample input during periods of abnormal activity as desired.

Another object of this invention is to provide a recorder of the type described which permits variations in the times at which samplings of electrocardiographic activity are to be taken and also permits changes in the durations of the intervals during which the activity is being monitored to suit the cardiac condition of the particular individual.

Still another object of this invention is to provide a recorder of the type described which can record electrocardiographic data and then can be operated to play the recorded data through an ECG recorder for analysis in the customary manner to permit immediate evaluation of the state of the individual's health with reference to the cardiac response sensed and recorded when the recorder is being worn on the person.

Other objects of this invention will become apparent as the following specification progresses, reference being had to the accompanying drawing for an illustration of the concepts of the invention.

IN THE DRAWINGS

Figure 2:
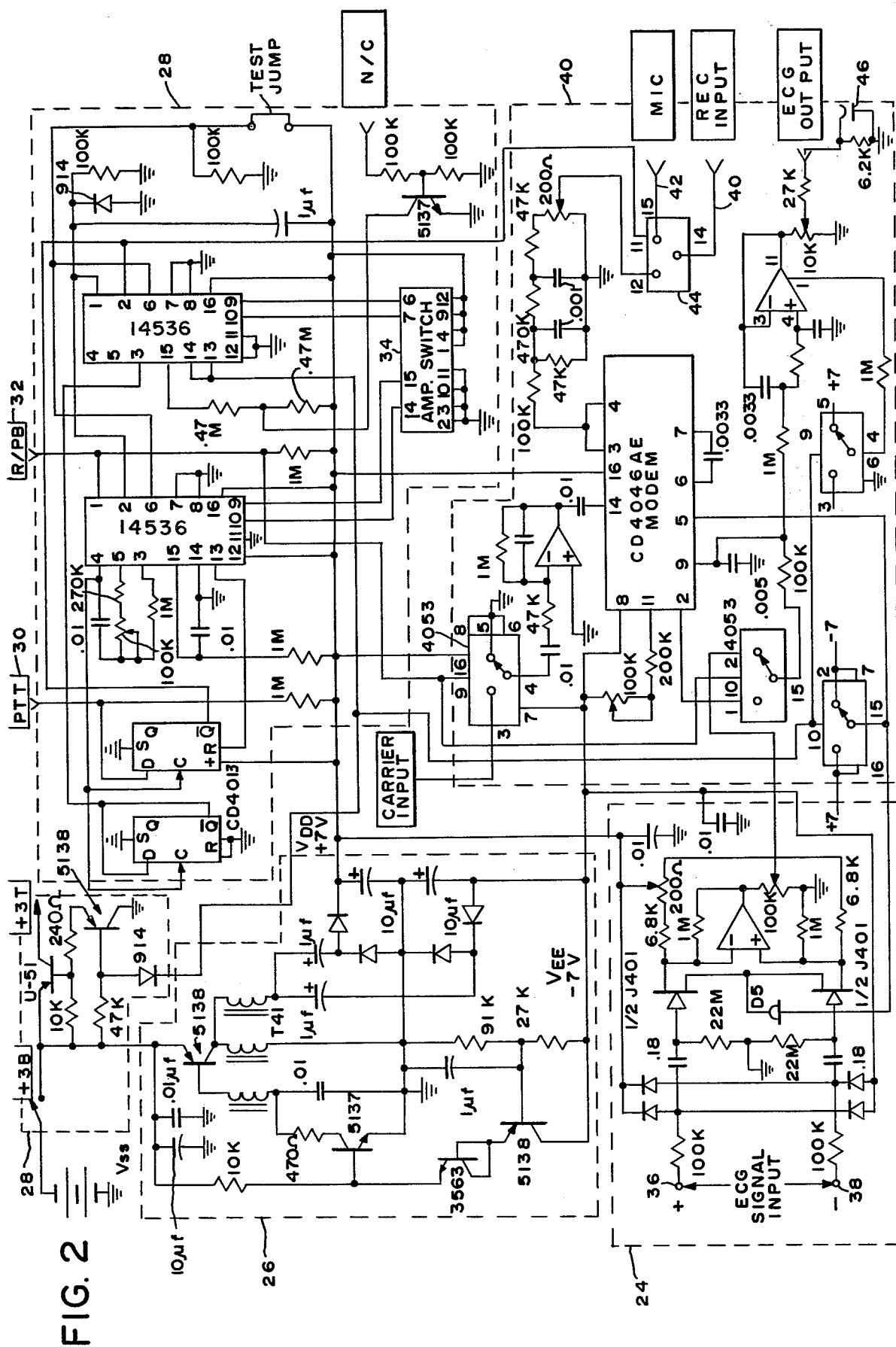

FIG. 1 is a block diagram of the system with the tape recorder and the program module forming the subject of the present invention; and FIG. 2 is a schematic diagram of the program module.

The present invention is directed to a system 10 which includes a data recorder which, for purposes of illustration, will be hereinafter described as a minature tape recorder 12 which is battery operated and can be carried on the person. The recorder has a signal input terminal 14 and a signal output terminal 16, whereby input signals can be directed to the recorder for recording thereon and signals recorded thereon can be played back to another recorder, such as an ECG recorder 17.

A program module 18 is associated with recorder 12 and includes a logic unit 20, a carrier modulator/demodulator or modem 22, an ECG amplifier 24 and a power converter 26. A control 28 for recorder 12 is also part of the program module, the latter being typically on a single circuit board carried on or within tape recorder 12. A more detailed circuitry of module 18 is shown in FIG. 2.

Logic unit 20 provides the programming means by which the recorder is turned on and off to control the frequency of data sampling periods and by which, when the recorder is on, to control the duration of each data sampling period. The details of logic unit 20 are shown in FIG. 2, wherein the logic is provided with a push-to-talk switch 30 to permit a microphone input to the tape recorder, such as during periods of abnormal cardiac activity. Also, a record/playback switch 32 is provided on logic unit 20 to permit the user to operate the recorder during time periods in which the program has the recorder normally turned off. Switches 30 and 32 are mounted on the tape recorder housing in accessible positions so that they can be readily actuated by the patient.

A 16-position switch 34 forming a part of logic unit 20 controls the frequency of data sampling periods and the duration of each such period. Means (not shown) can be provided for manually changing these times. To this end, a pair of adjustment screws or manually actuated stepper switches can be located in accessible positions on the tape recorder.

The input to amplifier 24 includes a pair of terminals 36 and 38 which are coupled to respective electrodes 39 and 41 (FIG. 1) attachable to the body of the user. One electrode can be, for instance, at the munubrium position and another electrode can be at the V-5 right position on the person. A third electrode 43, being the ground electrode, can be at any point on the body.

The output of the amplifier is directed to the modulator/demodulator 22 where it modulates a carrier signal, and the carrier signal is applied to the output terminal 40 coupled to the signal input terminal 14 of the recorder. The microphone input 42 is coupled to switch 44 and can be switched into electrical contact with terminal 40 for permitting voice signals to be recorded when the push-to-talk switch 30 is actuated.

Program Switch 34 (FIG. 2) may be a 16-position switch which controls both the intervals and duration of the programmed recording periods which may be according to the following table of switch positions:

| SAMPLE INTERVAL | SAMPLE DURATION (SECONDS) | | | |
|---|---|---|---|---|
| | 3.5 | 7 | 14 | 28 |
| 15 | 0 | 4 | 8 | C |
| 30 | 1 | 5 | 9 | D |
| 60 | 2 | 6 | A | E |
| 120 | 3 | 7 | B | F |

Pins 14 and 15 of switch 34 control the operation of the programmable interval counter 14536 by means of a binary code whereby the pins are either at ground or +7V potential, providing 00, 01, 10, or 11 combinations corresponding to the 15, 30, 60 and 120 minute intervals. Similarly, pins 6 and 7 of switch 34 control a second programmable counter (14536) which determines the durations of the samples initiated at the end of the programmed intervals.

The clock frequency driving both counters is provided by a section of each interval counter which is activated by components connected to pins 4 and 5 which determine the clock frequency of 145.6 Hz. Additional samples can be activated at any time by the user without affecting the programmed series by momentary activation of the PTT Switch 30. This switch, when released, triggers the duration counter, which through pins 13 and 14, turn on the record system elements for the programmed duration.

While the PTT switch 30 is held in the depressed position, the REC INPUT signal line 40 is connected through the gate 44 to the microphone, and the voice recording is made possible. At other times, the REC INPUT line 40 is connected to the MODEM carrier signal output filter.

The CD 4046 AE MODEM is a phase-locked loop oscillator which is used both as a voltage controlled oscillator to produce the frequency modulated carrier with a center frequency of 1700 Hz (in the RECORD mode), and as a carrier demodulator to produce a voltage proportioned to the carrier input signal in the PLAYBACK mode. During RECORD, the voltage from the ECG amplifier is fed through the 4053 gate to pin 9 of the MODEM, and a carrier signal is produced at pins 3 and 4 which is frequency modulated by that voltage. The center frequency is determined by the R-C values of the components between pins 8 and 11 and 6 and 7 of switch 34.

During PLAYBACK of the recorded tape, the CARRIER INPUT is routed through the 4053 gate and an isolation amplifier to pin 14 of the MODEM, and the voltage at pin 9 is controlled by the phase-lock loop action of the MODEM, which oscillates in phase with the incoming carrier signal. Thus, the ECG OUTPUT at 46 is provided by the ECG amplifier during RECORD and by the MODEM during PLAYBACK.

The input signals applied to amplifier 24 are channeled directly to an ECG output terminal 46 where an ECG recorder can be coupled to record the cardiac activity directly during the record cycle.

Modulator/demodulator 22 can be used for playback purposes by receiving the recorded signals from the tape by actuating switch 32. Such signals are then demodulated and applied as originally recorded to an ECG recorder for recording thereon in the customary manner. Thus, system 10 includes playback and demodulating circuitry which is self-contained, eliminating the need for any special equipment in the playback process.

System 10 is highly adapted to sense and record an ambulatory patient's ECG data upon demand and upon various programmed intervals over an extended period of time, such as 72 hours or more. The system is especially suitable for evaluation of transient cardiac abnormalities which involve symptoms apparent to the patient, such as angina, dyspnea, dizziness, fainting and the like, but which occur so infrequently that detection is unlikely during a brief stay in the doctor's office or hospital. A patient complaining of such symptoms can begin a recording of his cardiac data during an attack by momentarily depressing a pushbutton switch 30 and can shortly thereafter actuate push-to-talk switch 30 to record verbal remarks immediately following the sampling of the cardiac activity to give an exact correlation of the system with the recorded cardiac data.

These recordings can be played back into any office ECG recorder to obtain high fidelity ECG records without any additional equipment being required; thus, permitting a physician to rapidly determine whether such transient symptoms are attributable to cardiac irregularities and, if so, the type of irregularity involved.

If a history of the ECG action both before and after certain patient activity is desired, a continuous recording, up to 30 minutes or longer, can be made, with the patient starting and stopping the recording whenever desired. Typically, the recorder can be programmed to turn on for periods of 3½, 7, 14 or 28 seconds at intervals of 15, 30, 60 or 120 minutes throughout a day. Since one side of the tape of a typical tape recorder is capable of recording for 30 minutes, the recorder will continue to operate on such programs for approximately 15 hours at the maximum demand settings and for a week or more at the lower demand settings without changing either the tape or the batteries required to operate the recorder.

We claim:

1. A monitoring system for handling data representing cardiac activity comprising: sensing means including a number of electrodes for attachment to a human body to sense cardiac activity thereof and to provide data signals representing such activity; a portable recorder adapted to be carried on the person and having a recording medium for receiving and recording data signals when the recorder is actuated; a program module for interfacing the signals representing cardiac activity provided by the sensing means, said program module having a microphone input terminal and a manually actuated switch to enable the microphone input, said program module further including an amplifier for receiving and amplifying the data signals, a modulator for generating a carrier signal and modulating the carrier signal with the input data signals, means for applying the modulated signal to the recorder unit, a demodulator having a output terminal, and means coupling the demodulator to the recorder to permit demodulated signals to be applied to the output terminal for application to the input of an ECG recorder, there being first means coupled with the recorder for automatically actuating the same at the end of each of a sequence of time intervals and for keeping the recorder in an actuated state for a predetermined data sampling period each time it is actuated, said first means including means for changing the frequency of the time intervals and duration of the sampling periods; and second means including a manually actuated switch for actuating the recorder during any of said time intervals to permit recording of abnormal cardiac activity during such time interval, whereby data signals provided by the sensing means can be recorded on said medium for subsequent playback to permit the evaluation of the quality of the cardiac activity represented by the data signals.

* * * * *